(12) United States Patent
Ali

(10) Patent No.: US 10,782,281 B2
(45) Date of Patent: Sep. 22, 2020

(54) TISSUE MEASUREMENT DEVICE

(71) Applicant: Esah Ali, Flushing, NY (US)

(72) Inventor: Esah Ali, Flushing, NY (US)

( * ) Notice: Subject to any disclaimer, the term of this patent is extended or adjusted under 35 U.S.C. 154(b) by 124 days.

(21) Appl. No.: 15/783,569

(22) Filed: Oct. 13, 2017

(65) Prior Publication Data
US 2018/0313811 A1   Nov. 1, 2018

Related U.S. Application Data

(60) Provisional application No. 62/492,239, filed on Apr. 30, 2017.

(51) Int. Cl.
*G01N 1/00* (2006.01)
*G01N 33/483* (2006.01)

(52) U.S. Cl.
CPC .............................. *G01N 33/4833* (2013.01)

(58) Field of Classification Search
CPC ........................................................ G01N 1/00
See application file for complete search history.

(56) References Cited

U.S. PATENT DOCUMENTS

| 4,893,424 A | * | 1/1990 | McLean | G01N 1/36 264/158 |
| 7,888,132 B2 | * | 2/2011 | McCormick | G01N 1/31 422/404 |
| 2016/0157876 A1 | * | 6/2016 | Kim | A61B 17/072 227/178.1 |

* cited by examiner

*Primary Examiner* — Jyoti Nagpaul

(57) ABSTRACT

A device for containing and measuring a biological tissue specimen includes a tissue cassette with a ruler or metric device etched, printed, embossed, or designed into the cassette body. The device facilitates the measuring of a tissue specimen accurately, while reducing fatigue or contamination of the tissue sample.

12 Claims, 4 Drawing Sheets

TISSUE MEASUREMENT DEVICE

CROSS-REFERENCE TO RELATED APPLICATION

This application claims the benefit of priority of U.S. provisional application No. 62/492,239 filed on Apr. 30, 2017, the contents of which are herein incorporated by reference.

BACKGROUND OF THE INVENTION

The present invention relates to measurement of biological tissue, or more particularly, to a tissue cassette with tissue measuring capability.

Tissue cassettes are simple devices that hold biological tissue. They are generally made of plastic, have a chamber to house tissue, and a lid to contain the tissue. The tissue cassettes also have areas to label and read the description of contents, such as patient name, type of tissue, date collected or any other relevant information. Currently, doctors and lab technicians, use a standard metric ruler (plastic, wood, or metal) to obtain tissue measurements. This process involves movement and manipulation of tissue. This movement and manipulation have the risk of cross contaminating the tissue with other tissue, and is inefficient.

There exists a need for a device, which incorporates the functions of containing and measuring biological tissue. This merging of functions would improve compliance of technicians measuring tissue. It would also decrease cross-contamination and potential specimen mix-up caused by using a ruler during multiple specimen processing.

SUMMARY OF THE INVENTION

A cassette for holding and measuring a tissue sample includes a body including a bottom wall having an upper surface, and at least one side wall extending upwardly with respect to said bottom wall to define an interior space for receiving the tissue sample, a lid adapted to cover the body and be secured thereto in a closed position, and a ruler within the body to measure one or more dimensions of the tissue sample.

In one embodiment, the body includes a horizontal ruler and a vertical ruler. In one embodiment, the ruler measures in any measuring units that can measure the tissue sample.

In one embodiment, the ruler is made of flat markings on the body of the cassette. In one embodiment, the ruler is raised in the body. In an alternative embodiment, the ruler is embossed in the body. In one embodiment, the lid also includes a ruler on its surfaces.

In one embodiment, the lid includes a transparent window for viewing the tissue sample. The body can also include perforations. In one embodiment, the body includes a plurality of rulers positioned in a variety of orientations.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a tissue cassette with a ruler or metric device etched, printed, embossed, or designed into the molded body of the tissue cassette.

Figure 1:
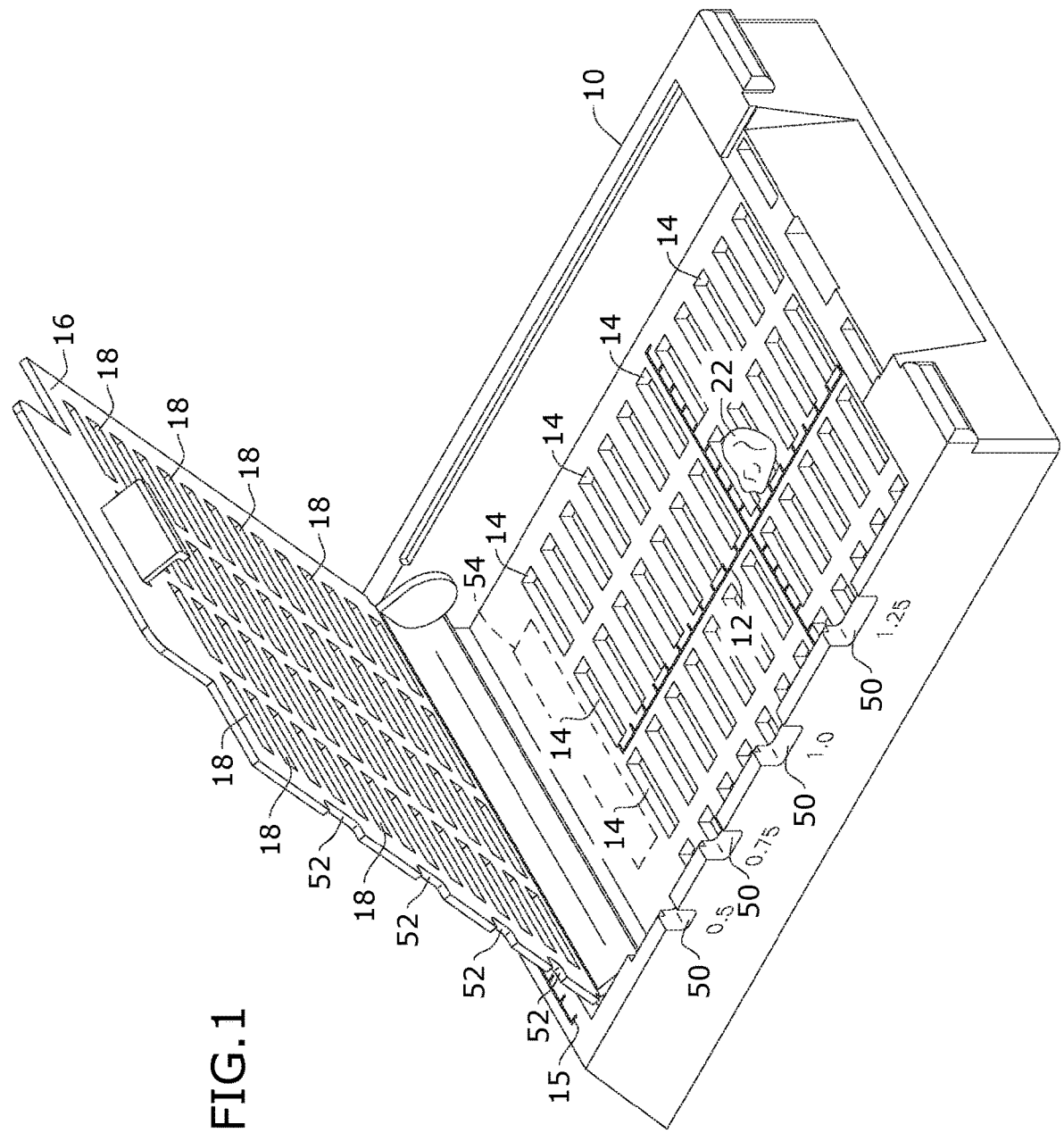
FIG. 1 is a perspective view of one embodiment of the invention shown in use.

As shown in the embodiment of FIG. 1, a tissue measurement device includes a cassette 10 with a lid 16. The cassette 10 includes holding slots 14 and the lid 16 includes a plurality of slots 18. Holding slots 14 assist in holding a tissue specimen 22 in place. Lid slots 18 act as grated vents for the tissue specimen.

The lid 16 includes lid notches 52 and cassette notches 50 to measure the diameter of cylindrical, hard tissue (for example, bone marrow core biopsies). The device includes a horizontal and vertical ruler 12 to measure tissue specimen 22. A distance between notches 50 is also marked with measurements. The cassette 10 also includes another ruler 15 for additional measurements if needed. In one embodiment, the ruler 15 is laser etched onto the cassette.

Figure 2:
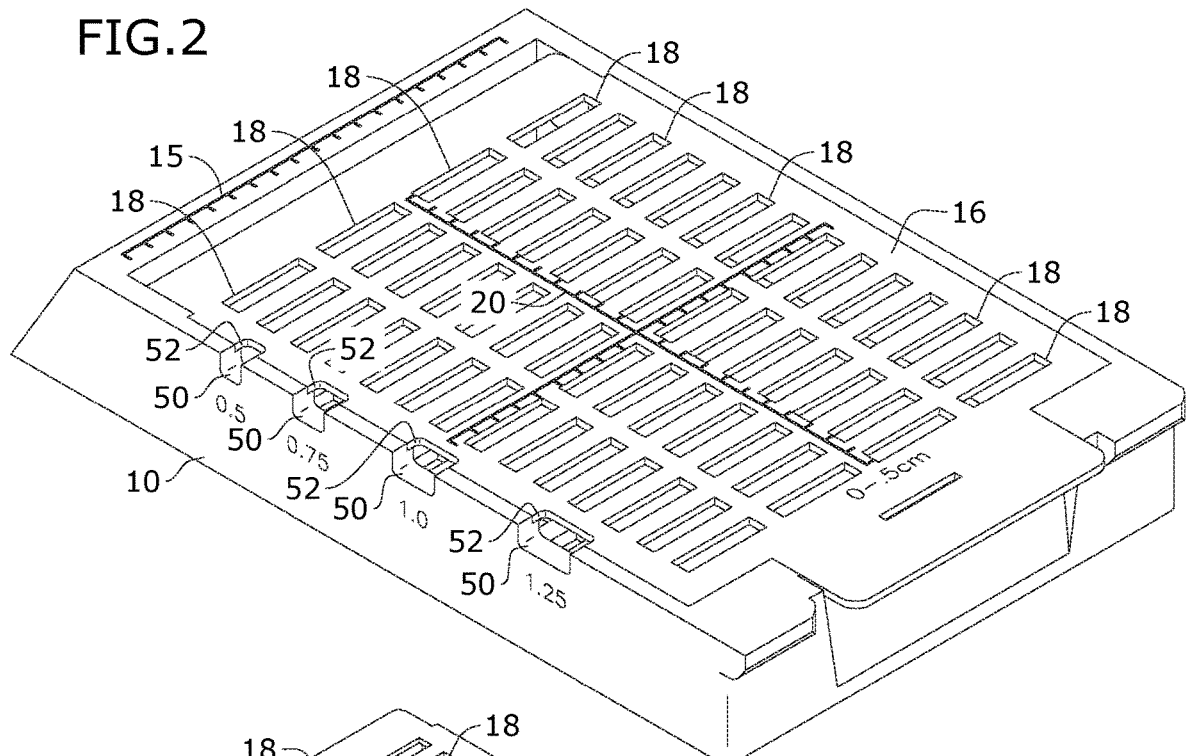
FIG. 2 is a perspective view of one embodiment of the invention.

A detailed view of the device when closed with lid 16 is shown in the embodiment of FIG. 2. The lid also has ruler 20 with a longitudinal ruler that measures ranges from 0-0.5 cm. In one embodiment, the distance between slots 14 is 0.1 mm. The ruler 12 assists marking this distance between the slots 14. It is to be understood that this range may be greater and smaller and in any measurement unit desired (inches, mm, etc.) Similarly, the horizontal axis range can be any desired range and in any desired units, depending on which unit ruler 20 is used. In this embodiment, the rulers 12 and 20 are printed on the respective cassette 10 and lid 16.

Figure 3:
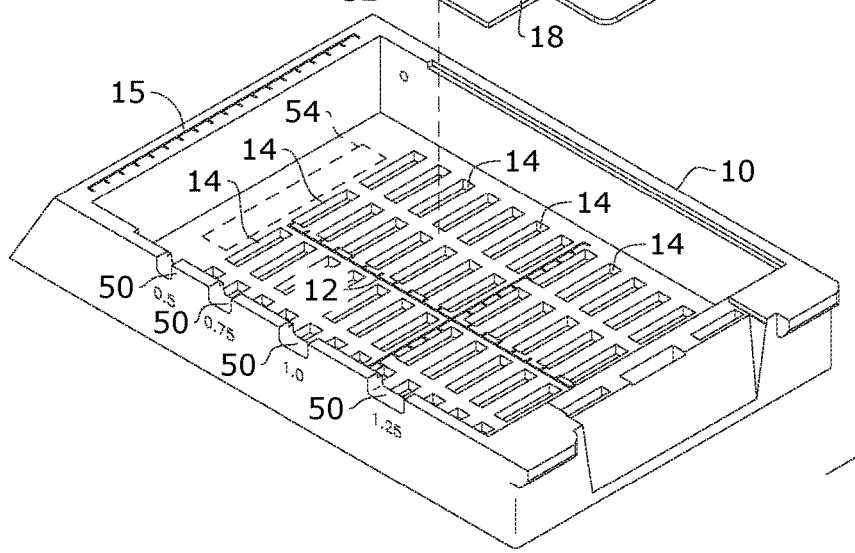
FIG. 3 is an exploded view of one embodiment of the invention.

As shown in the exploded view of FIG. 3, the ruler 12 of the cassette 10 is in the same position and of the same units and length as is the lid ruler 20 to ensure accurate measurement of a tissue sample. The cassette 10 and lid 16 are made of plastic or any other suitable material.

Figure 4:
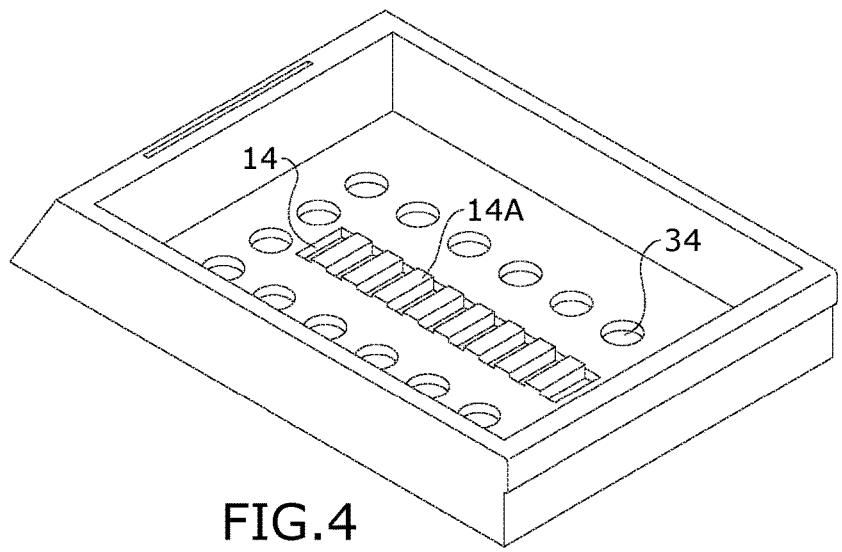
FIG. 4 shows one embodiment of the invention.

An alternative embodiment of the device is shown in FIG. 4. The cassette 30 includes slots 14 and ribs 14a. The cassette also includes holes 34. Each slot is about 1 mm in thickness and each rib is about 1 mm in thickness. The ribs and slots are used as a ruler to measure a tissue sample. In one embodiment, an additional ruler of up to 3 cm can be laser etched, printed, embossed, designed into the cassette body, or applied to the device by any suitable method.

In one embodiment, the cassette 30 includes a plurality of slots, each slot being about 1 mm in thickness and wherein a space between each slot is 1 mm in thickness. The slots and spaces are used as a ruler to measure a tissue sample.

Figure 5:
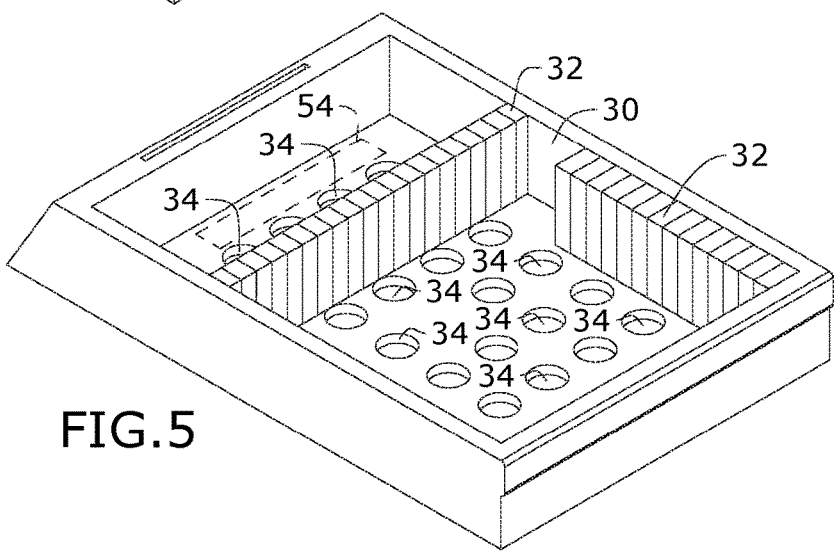
FIG. 5 is a perspective view of one embodiment of the invention.

FIG. 5 shows one embodiment of cassette 30. Cassette 30 includes holes 34 instead of slots. Cassette 30 further includes a raised ruler 32 with a horizontal ruler 32 and vertical ruler 32 for measuring a specimen. The cassette 30 includes an area 54 for placing a logo, trademark, or other desired information.

Figure 6:
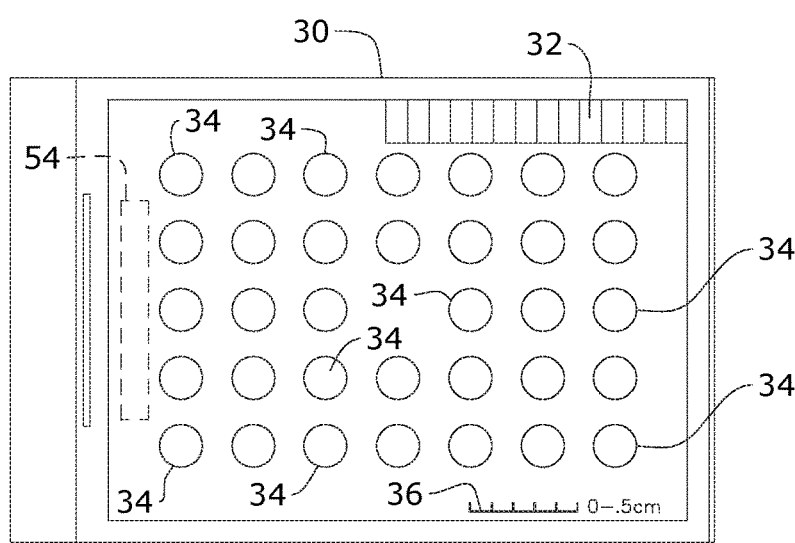
FIG. 6 is a top view of the embodiment of FIG. 5.

FIG. 6 shows a top view of cassette 30 with a flat or marked ruler 36 as an additional measurement tool.

Figure 7:
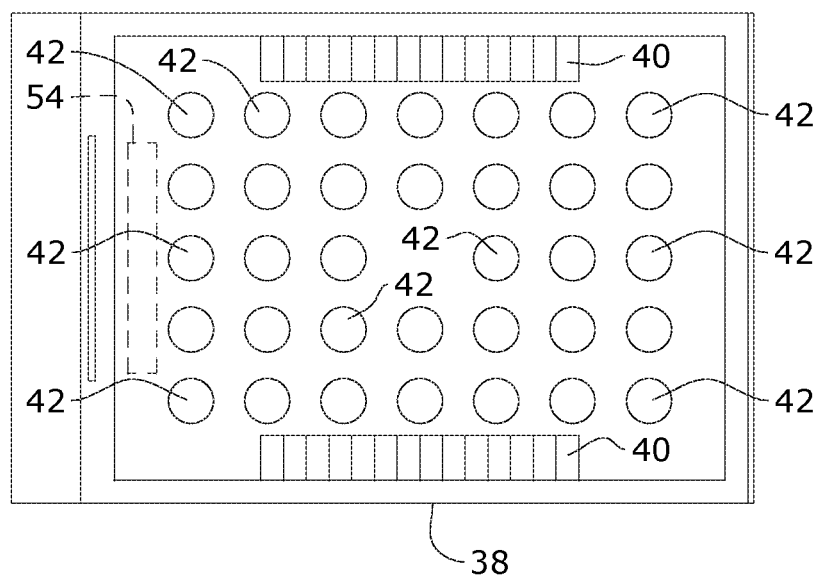
FIG. 7 is an alternative embodiment of the invention.

FIG. 7 shows an alternative embodiment of a cassette cover 38 with holes 42 and an embossed ruler 40. In one embodiment, the cassette cover 38 includes both horizontal or vertical rulers 40.

Figure 8:
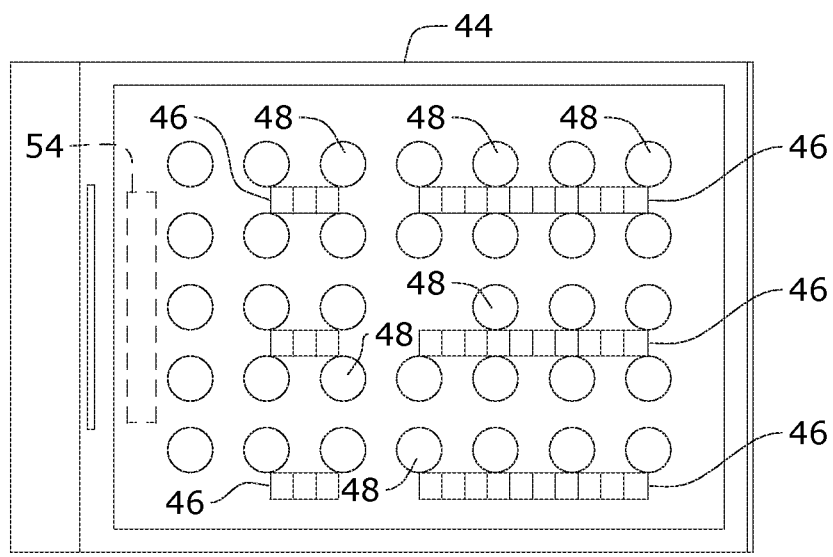
FIG. 8 is an alternative embodiment of the invention.

FIG. 8 shows a top view of an alternative embodiment of a cassette 44. The cassette cover includes holes 48 with a plurality of raised rulers 46 between rows of holes 48. This allows measurement of a specimen with a ruler proximal to the holes 48.

To use the device, a user handling small species removes the pieces of biopsied tissue from a specimen transport jar and places the tissue against the ruler of the cassette. The user simply records the measurement or uses it as needed.

In an alternative embodiment, the device works with digital cameras and other forms of media with built in algorithms (electronic rulers). For example, a digital camera mounted above the cassette on a grossing station captures an image similar to FIG. 1 with specimen 22. This image of specimen 22 is superimposed on a ruler 12 and can be automatically transcribed into a pathology report which, by standard, details the description and dimension of the specimen within the cassette. Hence, the built-in ruler or measuring device in the cassette is a vital component to improving and innovating future digital laboratories.

In an alternative embodiment, the device's physical and manual ruler 12 in FIG. 1, operates in conjunction with a digital camera electronic "software" ruler. The ruler 12 acts as a "back up" to ensure calibration of digital "algorithm" rulers on camera software.

Advantageously, the measurement feature of the described device simplifies the measurement of a specimen. Also, it guarantees compliance with measuring the tissue specimen in high volume operations, since it reduces fatigue and extra steps with using standard rulers. It further increases the accuracy of such tissue measurements.

Further, rulers used separately can result in contamination of the specimen, and are often inaccurate due to user variability or inconsistency for each procedure or measurement. The user often cannot accurately measure due to ergonomic stresses or using a ruler for each cassette.

It is to be understood that the ruler or measuring markers can be laser etched, printed, embossed, designed into the cassette body, or applied to the device by any suitable method, whether manually or by machine. The device also includes any number of rulers or measuring markers in any desired orientations and in any measuring units deemed suitable.

It should be understood that though the device is described as measuring biological tissue, it also extends to other commercial devices, where said devices incorporate the functions of precision measurement and containment in one device or process. Uses of these devices can have practical utility within the fields of manufacturing and engineering.

It should be understood, of course, that the foregoing relates to exemplary embodiments of the invention and that modifications may be made without departing from the spirit and scope of the invention as set forth in the following claims.

What is claimed is:

1. A cassette for holding and measuring a tissue sample, comprising:
   a body including a bottom wall having an upper surface, and at least one side wall extending upwardly with respect to said bottom wall to define an interior space for receiving the tissue sample;
   a plurality of cassette notches spaced apart along an upper surface of the at least one side wall;
   a lid adapted to cover the body and be secured thereto in a closed position;
   a plurality of lid notches spaced apart along an edge of the lid, wherein said pluralities of notches align in the closed position to define a plurality of successively larger spans to measure one or more diametric dimensions of the tissue sample;
   a ruler within the body to measure one or more linear dimensions of the tissue sample, the ruler being built into the body.

2. The cassette of claim 1, wherein the body includes a horizontal ruler and a vertical ruler.

3. The cassette of claim 1, wherein the ruler measures in any measuring units that are capable of measuring the tissue sample.

4. The cassette of claim 1, wherein the ruler is made of flat markings on the body.

5. The cassette of claim 1, wherein the ruler is raised in the body.

6. The cassette of claim 1, wherein the ruler is embossed in the body.

7. The cassette of claim 1, wherein the lid includes a ruler on its surface.

8. The cassette of claim 1, wherein the body includes perforations.

9. The cassette of claim 1, wherein the body includes a plurality of rulers positioned in a variety of orientations.

10. The cassette of claim 1, wherein the ruler includes a plurality of slots, each slot being 1 mm in thickness and wherein a space between each slot is 1 mm in thickness.

11. The cassette of claim 1, wherein the ruler includes a plurality of slots and a plurality of ribs, each slot being 1 mm in thickness and each rib being 1 mm in thickness.

12. The cassette of claim 1, wherein the ruler includes a plurality of slots and a plurality of ribs, and wherein the ruler occupies a central part of the cassette and is 3 cm in length.

* * * * *